(12) United States Patent
Grüll et al.

(10) Patent No.: US 6,235,505 B1
(45) Date of Patent: May 22, 2001

(54) PROCESS FOR THE PRODUCTION OF CYCLODEXTRIN

(75) Inventors: Dietmar Grüll, Langenschönbichl; Ulrich Stifter, Klosterneuburg, both of (AT)

(73) Assignee: Südzucker Aktiengesellschaft, Mannheim/Ochsenfurt (DE)

( * ) Notice: Subject to any disclaimer, the term of this patent is extended or adjusted under 35 U.S.C. 154(b) by 0 days.

(21) Appl. No.: 09/372,308

(22) Filed: Aug. 11, 1999

(30) Foreign Application Priority Data

Aug. 11, 1998 (AT) ..................................................... 1380/98

(51) Int. Cl.[7] .......................... C12P 19/16; C12P 19/00; C12P 19/44
(52) U.S. Cl. .................... 435/98; 435/72; 435/74
(58) Field of Search .................. 435/72, 74, 98; 260/536

(56) References Cited

U.S. PATENT DOCUMENTS 3,425,910   2/1969   Armbruster et al. ................... 195/31
4,477,568   10/1984  Hokse et al. ............................ 435/97

FOREIGN PATENT DOCUMENTS 60-188088 * 9/1985 (JP) .
9211376 * 7/1992 (WO) .
93/10255 5/1993 (WO) .

OTHER PUBLICATIONS

Ronald C. Deis: "Food Product Design—The New Starches", Feb. 1998, Weeks Publishing Co., Northbrook, IL 60062.
Rendlemab et al., Biotechnol. Appl. Biochem., 26, 51–61, Aug. 1997.*

* cited by examiner

Primary Examiner—Ponnathapu Achutamurthy
Assistant Examiner—Maryam Monshipouri
(74) Attorney, Agent, or Firm—Herbert L. Lerner; Laurence A. Greenberg; Werner H. Stemer

(57) ABSTRACT

Disclosed is the use of amylopectin potato starch obtained from potatoes whose amylose formation is inhibited through breeding, or through genetic engineering or other molecular biological processes, as starting material for a process for production of cyclodextrin from potato starch by reaction with cyclodextrin glycosyltransferase. This starch starting material combines the positive effects of natural amylopectin starch with those of potato starch and is distinguished, among other properties, through low lipid and protein content and therefore higher purity. The yield of cyclodextrins is surprisingly high. In this way cyclodextrin can be produced at much lower cost than previously and can therefore be used for the first time on a larger scale in technical processes.

19 Claims, No Drawings

PROCESS FOR THE PRODUCTION OF CYCLODEXTRIN

BACKGROUND OF THE INVENTION

FIELD OF THE INVENTION

The subject of this invention is a process for the production of cyclodextrin from amylopectin potato starch by reaction with cyclodextrin glycosyltransferase (CGTase, also known as cyclodextrin transglycosylase, EC No. 2.4.1.19).

The name cyclodextrins refers to a group of substances whose molecules consist of several anhydroglucose units with cyclically linked alpha-1,4-glucosidic bonds, whereby the smallest cyclodextrin, alpha-cyclodextrin, contains 6 glucose units. A distinction is also made between beta- and gamma-cyclodextrin according to the number of anhydroglucose units in the ring which is formed. Beta-cyclodextrin is the thermodynamically favored product in the conversion of starch to cyclodextrin by means of CGTase. The higher-ring cyclodextrins are preferred for technical applications.

Up to now the following starches have been used as the main starting materials in technical processes for producing cyclodextrins:

Potato starch: the potato can be grown with high yields per hectare even in unfavorable locations. It has low protein and lipid contents and therefore affords a very pure starch.

Maize and waxy maize starch: maize requires a warmer climate. Waxy maize ripens in high proportions. It must be grown in favorable locations with adequate separation from normal maize. Low yields per hectare lead to a further cost increase.

A considerable disadvantage for starch from maize and waxy maize is the high protein and lipid content (necessitating complicated and costly purification of the starch).

Wheat starch: is a poorer substrate than potato or maize starch since the yield of cyclodextrin that can be produced from it is much lower.

The usual natural starches are a mixture of the two forms of starch, amylopectin and amylose. Amylose and amylopectin are not single substances but mixtures of polymers with different molecular weights and different glucose linkages. Amylose consists mainly of straight-chain polysaccharides in which the glucose units are joined by alpha-1,4-linkages. Amylopectin, on the other hand, is a highly branched glucose polymer in which the glucose units are joined through 1,6-linkages at the branching positions in addition to the alpha-1,4-linkages. It has been found that amylopectin forms more stable solutions than amylose because amylose has a tendency towards unwanted retrogradation, i.e. the recombination of chains which have already been separated from one another.

The usual natural starches contain 15% to 30% amylose irrespective of the type of plant they have been obtained from. Only maize varieties of the so-called waxy type provide a starch which consists almost exclusively of amylopectin. In rare cases a starch rich in amylopectin can also be obtained from so-called waxy rice or waxy barley.

Amylose and amylopectin can be separated from each other by fractionation. These processes are very complicated and cost-intensive and are hardly ever used except on a laboratory scale. Furthermore, fractionation of natural starches leads to uncontrolled degradation and damage to the starch fractions with impairment of the properties of the final products.

For this reason amylopectin starch is hardly ever used for technical purposes. The only use in practice involves a certain amount of waxy maize starch in the food industry because this generates a more pleasant feeling in the mouth than does usual starch.

The production of cyclodextrin from starch is the subject of many publications in the literature. Thus U.S. Pat. No. 3,425,910 describes a process for the production of cyclodextrin from a starch hydrolysate. The use of potato starch as starch starting material is mentioned. At the time of filing of the above US patent (1966) potato starch is a usual starch with an amylose content of approximately 20% by weight.

In PCT application WO 93/10255 the production of cyclodextrin from a starch containing at least 90% amylopectin is described whereby it is stated that the cyclodextrin obtained gives a clear solution when dissolved in water. Preferred starch starting materials contain 95% amylopectin or more, preferably around 99%. Waxy maize starch, waxy rice starch and waxy barley starch are expressly stated to be the starting materials with waxy maize starch being preferred. Potato starch and maize starch with normal amylose content are named in Example 1 as comparison starches for demonstrating the positive effects of using waxy maize starch.

Among the process conditions listed in the above PCT application is the use of a complexing agent for cyclodextrin for the purpose of better separation of same from the reaction medium. Toluene, 1-decanol, cyclodecanol, cyclohexane, trichloroethylene, tetrachloroethane, bromobenzene, 2,3-cyclododenopyridine, naphthalene, 1-naphthol, 2-naphthol and dimethylphenol are named as complexing agents.

An overview of the industrial production of cyclodextrins is provided in J. Szejtli and T. Ose, Comprehensive Supramolecular Chemistry, Vol. 3, Cyclodextrins, 1996, Pergamon, Oxford, UK, in Article 3 on Page 41, Preparation and Industrial Production of Cyclodextrins, G. Schmid, Wacker-Chemie GmbH, Munich, Germany.

A description is given of the different conversion conditions and their influence on the ratio of alpha-, beta- and gamma-cyclodextrin. In this connection the addition of a special complexing agent during the production process can also modify the relative proportions of the three kinds of cyclodextrin.

It is also mentioned that the alpha-1,6-glucoside linkages at the branching positions in amylopectin block the effect of CGTase. If amylopectin is treated with debranching enzymes such as pullulanase or isoamylase before the addition of CGTase the level of conversion of the starch into cyclodextrin is increased by several percent.

It is also subsequently mentioned in the above Szejtli and Ose publication that amylopectin is a better substrate than amylose for the production of cyclodextrin because the reaction with CGTase begins at the non-reducing end of the starch molecule. Since amylopectin has considerably more non-reducing ends than amylose, the level of conversion is higher when amylopectin is used. It is therefore recommended that potato starch be used instead of maize starch because potato starch has an intrinsically higher amylopectin content than maize starch (approximately 79% for potato compared with approximately 72% for maize).

Finally, the attempt is also described to produce cyclodextrin directly in the tubers of transgenic potato plants through construction of a chimeric gene by means of the CGTase gene from Klebsiella oxytoca. It did in fact prove possible to detect small amounts of cyclodextrin in the potato tubers. Extraction of the tuber tissue was performed using a C18 Sep-pak column which binds the cyclodextrin but not the starch.

U.S. Pat. No. 4 477 568 mentions among other things the use of fractionated amylopectin starch from a wide variety of crops, e.g. maize, wheat, sorghum, potato, tapioca, sago and rice, for the production of cyclodextrin.

However, since the starch fractionation processes have not been generally accepted for the above reasons, the search is still going on for a cyclodextrin starting material which does not have the disadvantages listed.

SUMMARY OF THE INVENTION

It is accordingly an object of this invention to provide a process for the production of cyclodextrin that overcomes the above-mentioned disadvantages of the prior art methods and enables cyclodextrin to be produced economically for technical applications.

With the foregoing and other objects in view there is provided, in accordance with the invention, a process in which amylopectin potato starch obtained from potatoes with amylose formation inhibited as a result of breeding or of molecular biological/genetic engineering procedures is used as the starting material in a process for the production of cyclodextrin from amylopectin potato starch by reaction with cyclodextrin glycosyltransferase.

Recent years have seen the successful development of genetic modification of potatoes with the aim of producing starch which is practically free of amylose. The amylopectin potato starch obtained from such potatoes combines the advantages of an almost pure amylopectin possessing the original properties of the natural product, with the advantages of potato starch, namely its low lipid and protein content.

Also in accordance with this invention, the amylopectin potato starch is best obtained from potatoes in which amylose formation is inhibited by such molecular biological/genetic engineering procedures as anti-sense technique or cosuppression. These procedures are well known in the art and need no further explanation.

Additional molecular biological procedures to inhibit amylose synthesis include processes based on mutation of the potato plant.

The amylose-inhibited potato varieties used as producers of amylopectin starch starting material for the process of the invention provide an amylopectin starch with an amylopectin content of above 90% by weight, preferably above 95%. For the process according to the invention an amylopectin potato starch with an amylopectin content of above 98% is especially preferred.

Determination of the amylose content and the amylopectin content of a starch is carried out according to: J. H. M. Hovenkamp-Hermelink, J. N. DeVries, F. Adamse, E. Jacobsen, W. Witholt and W. J. Feenstra, "Rapid estimation of the amylose amylopectin ratio in small amounts of tuber and leaf tissue of the potato", Potato Res., (1988), 241–246.

The enzyme cyclodextrin glycosyltransferase (EC No. 2.4.1.19) is produced by cultivating micro-organisms which produce this enzyme and extracting the enzyme from the fermentation broth. B. macerans is an example of such a micro-organism.

Because of the internal cavity they possess, cyclodextrins form inclusion compounds or complexes with diverse smaller molecules or monomers. It may be assumed that this complex formation proceeds through the hydrophobic interaction between the non-polar inside of the cyclodextrin ring and the non-polar guest molecule, together with van der Waals forces. As a result of this inclusion within the cyclodextrin, the chemical and physical properties of the guest molecule are altered to such an extent that specific modifications to the guest molecule can be carried out.

Among the advantageous effects of complexation with cyclodextrin are the following:
 1. Stabilization of substances sensitive to light or oxygen.
 2. Modification of the chemical reactivity of guest molecules:
    a) reactive substances are protected by inclusion and can be mixed safely with other substances;
    b) the selectivity of reactions can be influenced through inclusion of functional groups;
    c) reactions can be promoted or suppressed.
 3. Fixation of volatile substances:
    a) storage and manipulation is facilitated, especially with toxic substances;
    b) smaller quantities of volatile substances are necessary since evaporation losses are reduced;
    c) aroma substances and physiologically active substances can be better dosed.
 4. Modification of application-related properties of the guest molecules:
    a) substances difficult to dissolve in water dissolve more easily on addition of cyclodextrin and can be more easily emulsified;
    b) powdered, freeze-dried cyclodextrin complexes are finely dispersed and dissolve more easily noncomplexed guest molecules difficult to dissolve in water;
    c) pigments can be masked or the color of a substanc can be altered since the absorption spectrum normally changes on inclusion;
    d) unpleasant tastes can be suppressed.

A future increase in the use of cyclodextrins can be expected, particularly in the food industry, if their production costs can be reduced.

DESCRIPTION OF PREFERRED EMBODIMENTS

The amylopectin potato starch according to the invention can be used as obtained from potatoes, untreated, or pretreated mechanically, thermally, chemically and/or enzymatically. Such pretreatment serves to liquefy or improve the solubility of the starch.

Mechanical pretreatment involves liquefying the amylopectin potato starch by high-speed stirring.

The starch can also be treated thermally at temperatures up to approximately 155° C.

Chemical pretreatment normally involves treatment with acid, preferably with hydrochloric acid.

On the other hand, the starch can also be pretreated with oxidizing agents such as sodium hypochlorite.

If an amylopectin potato starch is treated with alphaamylase an enzymatic degradation takes place which also renders the starch easier to dissolve.

Chemical pretreatment for the production of starch ethers, esters and/or cross-linked starch products is also used to advantage.

It has also been found in accordance with the invention that treatment with a debranching enzyme such as pullulanase (EC 3.2.1.41) or isoamylase (EC 3.2.1.68) has a beneficial effect on the yield of the cyclodextrin.

According to a further feature of this invention, the use of a complexing agent is also beneficial in the process to the invention.

Table 1 below shows the increase in yield of cyclodextrin (CD) by the use of pullulanase and by the use of pullulanase together with a complexing agent (AP=amylopectin).

The starch suspension is pretreated at 100° C.; the cyclization reaction then proceeds at 25° C.

TABLE 1

| Substrate used | Yield of CD (%) | Yield using pullulanase (%) | Yield using pullulanase and complexing agent (%) |
|---|---|---|---|
| Fract. maize AP | 22.6 | 36.1 | 89.8 |
| Maize starch | 14 |  | 87.2 |
| Waxy maize starch | 18.6 |  | 90.6 |
| Potato starch | 18.9 |  | 85.9 |
| Potato AP from transgenic potato | 25.1 | 38.3 | 92.3 |
| Wheat starch | 15.8 |  | 86.9 |

Without intending to be limited by any theory, the following may explain why the highest yields of cyclodextrins are obtained from amylose-free potato starch:

The use of isoamylase or pullulanase as debranching enzyme leads to the production of fragments with chain lengths of DP 60 and 18. Table 2 below shows the DP distribution of different amylopectins debranched using isoamylase.

TABLE 2

| Amylopectin | DP Fraction 1 | DP Fraction 2 | Weight ratio F1:F2 |
|---|---|---|---|
| Potato | 60 | 18 | 1:2.1 |
| Maize | 45 | 15 | 1:3.5 |
| Wheat | 49 | 13 | 1:4.8 |

The small fragment fraction is lowest for the potato starch (M. T. Kalichevsky, P. D. Orford and S. G. Ring, "The retrogradation and gelation of amylopectins from various botanical sources", Carbohyd. Res., 198 (1990) 49–55). The highest yields of cyclodextrins are obtained with starches of DE≦2 (F. C. Armbruster and E. R. Kool, Production of Cyclodextrin, U.S. Pat. No. 3,425,910).

The yields of cyclodextrins obtained using amylopectin starches from transgenic potatoes are higher than the yields obtained from reaction mixtures with waxy maize starch (J. W. Shieh and A. Hedges, PCT application WO 93/10255 (1993)). A possible explanation is the higher content of Fraction 1 dextrin with DP 60.

In accordance with an additional feature of the invention, it has been found particularly advantageous to use an amylopectin potato starch with a degree of polymerization level (DP) of ≧50. As can be seen in Table 3 below, the yield of cyclodextrin increases with increasing DP of the starch used as starting material.

TABLE 3

| Yield of cyclodextrin (%) | DP |
|---|---|
| 51.2 | 10 |
| 70.7 | 20 |
| 92.3 | ≧50 |

The high purity of the potato starch (low fat and protein content) is an advantage in isolation of the cyclodextrins from the reaction mixture, as manifested for example in an improved transmission. The protein and lipid contents of certain commercial starches are listed in Table 4:

TABLE 4

| | % in dry substance | |
|---|---|---|
| Starch | Protein | Lipid |
| Maize | 0.2–0.4 | 0.5–0.9 |
| Potato | 0.05–0.1 | 0–0.1 |

The following Example is offered by way of illustration and not of limitation.

EXAMPLE 100 g of amylose-free potato starch from transgenic potato was suspended in 1 litre of water and gelatinized by heating to 100° C. within 30 minutes. After cooling to 25° C. either 16.5 ml of pullulanase suspension (45 U/ml) or 0.5 ml of isoamylase suspension (5330000 U/ml) was added, pullulanase as suspension in ammonium sulfate solution (1 unit liberates 1 micromol of maltotriose from pullulan/min at pH 5.0 and 25° C.) and isoamylase as suspension in 2.0 M ammonium sulfate solution (1 unit causes, after 15 min at room temperature, an increase in $A_{610}$ of 0.1 in a solution prepared as follows: After incubation of a mixture of 0.5 ml of 1% soluble rice starch, 0.1 mol of 0.5 M acetate buffer [pH 3.6] and 0.1 ml of enzyme solution at 40° C. for 1h a 0.5 ml aliquot was then mixed with 0.05 ml of 0.01 M iodine/KI solution and diluted with water to 12.5 ml).

The mixture was stirred for 3 hours. 10 mg of cyclodextrin glycosyltransferase and cyclodecanone as complexing agent were then added. This reaction mixture was stirred for 10 days. A 92.8% yield of cyclodextrins was obtained when pullulanase was used.

We claim:

1. A process for the production of cyclodextrin from amylopectin potato starch in which amylopectin potato starch containing at least 90% amylopectin and obtained from potato having amylose formation inhibited, as a result of breeding or of genetic engineering or other molecular biological procedures, is reacted with cyclodextrin glycosyltransferase (EC No. 2.4.1.19), and cyclodextrin is isolated from the reaction mixture in enhanced yield and purity compared to an otherwise comparable process with fractionated amylopectin of maize starch as substrate.

2. The process according to claim 1, in which amylopectin potato starch is obtained from potatoes whose amylose formation is inhibited through use of anti-sense technique.

3. The process according to claim 1, in which amylopectin potato starch is obtained from potatoes whose amylose formation is inhibited through use of cosuppression.

4. The process according to claim 1, in which amylopectin potato starch with an amylopectin content of at least 95% is used.

5. The process according to claim 4, in which amylopectin potato starch with an amylopectin content of at least 98% is used.

6. The process according to claim 1, in which mechanically and/or thermally and/or chemically and/or enzymatically pretreated amylopectin potato starch is used.

7. The process according to claim 6, in which amylopectin potato starch is mechanically pretreated by high-speed stirring.

8. The process according to claim 6, in which amylopectin potato starch is thermally pretreated at temperatures up to approximately 155° C.

9. The process according to claim 6, in which amylopectin potato starch is chemically pretreated with acid.

10. The process according to claim 9, in which the acid is hydrochloric acid.

11. The process according to claim 6, in which amylopectin potato starch is chemically pretreated with an oxidizing agent.

12. The process according to claim 11, in which the oxidizing agent is sodium hypochlorite.

13. The process according to claim 6, in which amylopectin potato starch is enzymatically pretreated with alpha-amylase.

14. The process according to claim 6, in which amylopectin potato starch is chemically pretreated by etherifcation, esterification and/or cross-linking.

15. The process according to claim 6, in which amylopectin potato starch is enzymatically pretreated with a debranching enzyme.

16. The process according to claim 15, in which the debranching enzyme is isoamylase (EC 3.2.1.68) or pullulanase (EC 3.2.1.41).

17. The process according to claim 1, in which amylopectin potato starch has a $DP \geqq 50$.

18. The process according to claim 1, in which the conversion of the starch with CGTase is carried out in the presence of a complexing agent for cyclodextrin.

19. The process according to claim 18, in which the complexing agent is cyclododecanone.

* * * * *

UNITED STATES PATENT AND TRADEMARK OFFICE
CERTIFICATE OF CORRECTION

PATENT NO.   : 6,235,505 B1
DATED        : May 22, 2001
INVENTOR(S)  : Dietmar Grüll et al.

It is certified that error appears in the above-identified patent and that said Letters Patent is hereby corrected as shown below:

Title page,
Item [73], should read as follows:
-- Südzucker Aktiengesellschaft Mannheim/Ochsenfurt, Mannheim, Germany --

Signed and Sealed this

Thirtieth Day of April, 2002

Attest:

JAMES E. ROGAN
*Director of the United States Patent and Trademark Office*

*Attesting Officer*